US012594018B2

(12) United States Patent
Govari

(10) Patent No.: US 12,594,018 B2
(45) Date of Patent: Apr. 7, 2026

(54) METHOD AND SYSTEM FOR ASSISTING A USER IN GUIDING A CATHETER DURING A CARDIAL OPERATION

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 73 days.

(21) Appl. No.: 18/668,462

(22) Filed: May 20, 2024

(65) Prior Publication Data

US 2025/0352119 A1    Nov. 20, 2025

(51) Int. Cl.
| | |
|---|---|
| *A61B 5/343* | (2021.01) |
| *A61B 5/00* | (2006.01) |
| *A61B 5/0538* | (2021.01) |
| *A61B 5/06* | (2006.01) |
| *A61B 5/287* | (2021.01) |
| *A61B 18/00* | (2006.01) |

(52) U.S. Cl.
CPC ............ *A61B 5/343* (2021.01); *A61B 5/0538* (2013.01); *A61B 5/062* (2013.01); *A61B 5/287* (2021.01); *A61B 5/6853* (2013.01); *A61B 5/6858* (2013.01); *A61B 2018/00357* (2013.01); *A61B 2018/00577* (2013.01)

(58) Field of Classification Search
CPC ........... A61B 2018/00297; A61B 2018/00982; A61B 8/465
See application file for complete search history.

(56) References Cited

U.S. PATENT DOCUMENTS

| | | | |
|---|---|---|---|
| 5,391,199 | A | 2/1995 | Ben Haim |
| 5,443,489 | A | 8/1995 | Ben Haim |
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben Haim |

(Continued)

FOREIGN PATENT DOCUMENTS

WO    WO-2007059172 A2 *    5/2007    ............. G16Z 99/00

OTHER PUBLICATIONS

Extended European Search Report, received for European Application No. 24212487.3, mailed on Apr. 17, 2025, 10 pages.

*Primary Examiner* — Christopher Koharski
*Assistant Examiner* — Helene Bor

(57)    ABSTRACT

A method, apparatus and computer program product, the method comprising: obtaining electrical information from a plurality of electrodes disposed on a distal end assembly of a catheter within a heart of a patient as the catheter is being maneuvered within the heart; dynamically identifying a portion of the distal end assembly that is displaced from tissue wall of the heart, based upon the electrical information received from the plurality of electrodes; generating a visual representation of the distal end assembly; dynamically distorting the visual representation by warping (the identified portion of the distal end assembly; and rendering the visual representation as dynamically distorted to the display device.

20 Claims, 6 Drawing Sheets

(56)  References Cited

U.S. PATENT DOCUMENTS

| | | | |
|---|---|---|---|
| 6,788,967 | B2 | 9/2004 | Ben Haim |
| 6,892,091 | B1 | 5/2005 | Ben Haim |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |
| 8,456,182 | B2 | 6/2013 | Bar-Tal |
| 8,676,305 | B2 | 3/2014 | Hayam et al. |
| 9,629,567 | B2 | 4/2017 | Porath et al. |
| 2007/0124128 | A1* | 5/2007 | Connacher ............. G09B 23/30 |
| | | | 703/11 |
| 2010/0121139 | A1* | 5/2010 | OuYang ............. A61B 1/00181 |
| | | | 600/104 |
| 2014/0357956 | A1 | 12/2014 | Salahieh et al. |
| 2017/0333125 | A1 | 11/2017 | Lepak et al. |
| 2020/0022653 | A1* | 1/2020 | Moisa ................ A61B 18/1492 |
| 2022/0192753 | A1* | 6/2022 | Rosenberg ............. A61B 34/20 |
| 2022/0370145 | A1* | 11/2022 | Korgozki ............. G02B 27/017 |
| 2023/0028867 | A1* | 1/2023 | Buchnik ............ A61B 18/1492 |
| 2023/0157569 | A1 | 5/2023 | Govari et al. |
| 2023/0210437 | A1* | 7/2023 | Beeckler ................ A61B 5/367 |
| | | | 600/523 |

* cited by examiner

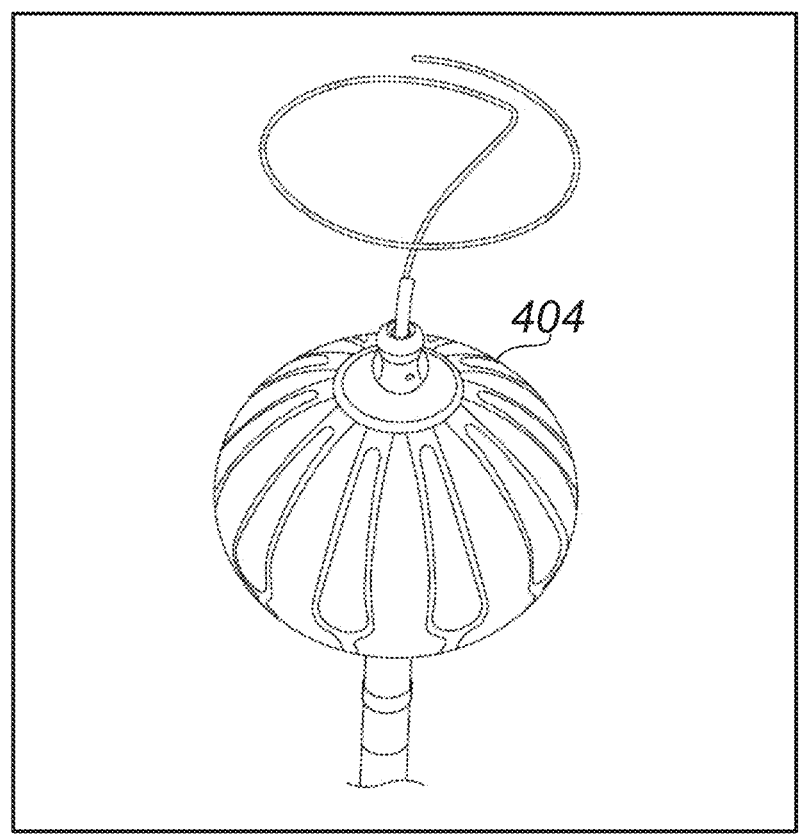
FIG. 4A
FIG. 4B
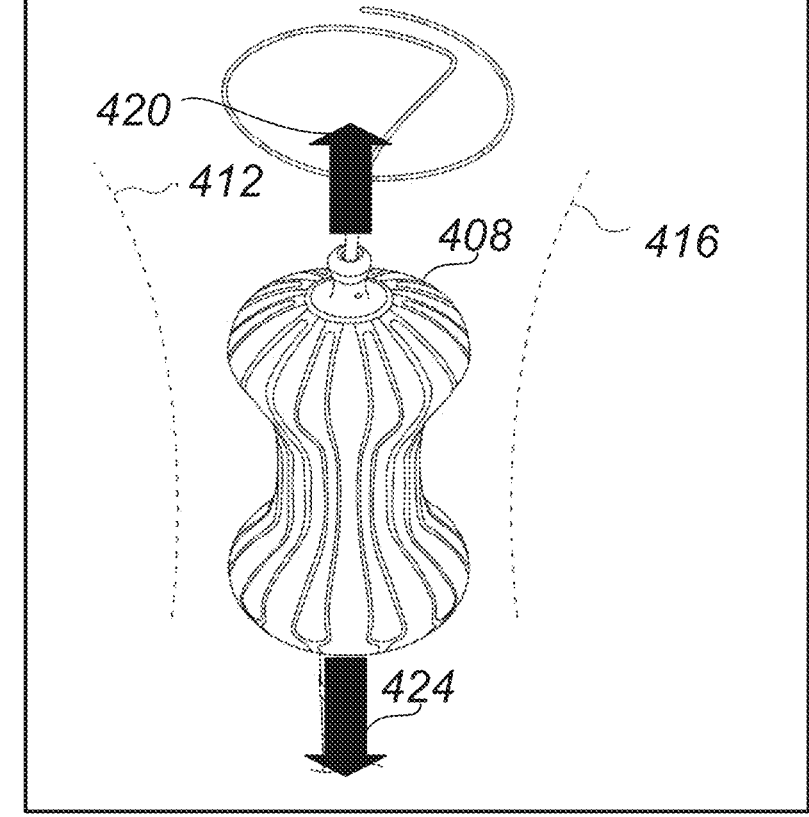

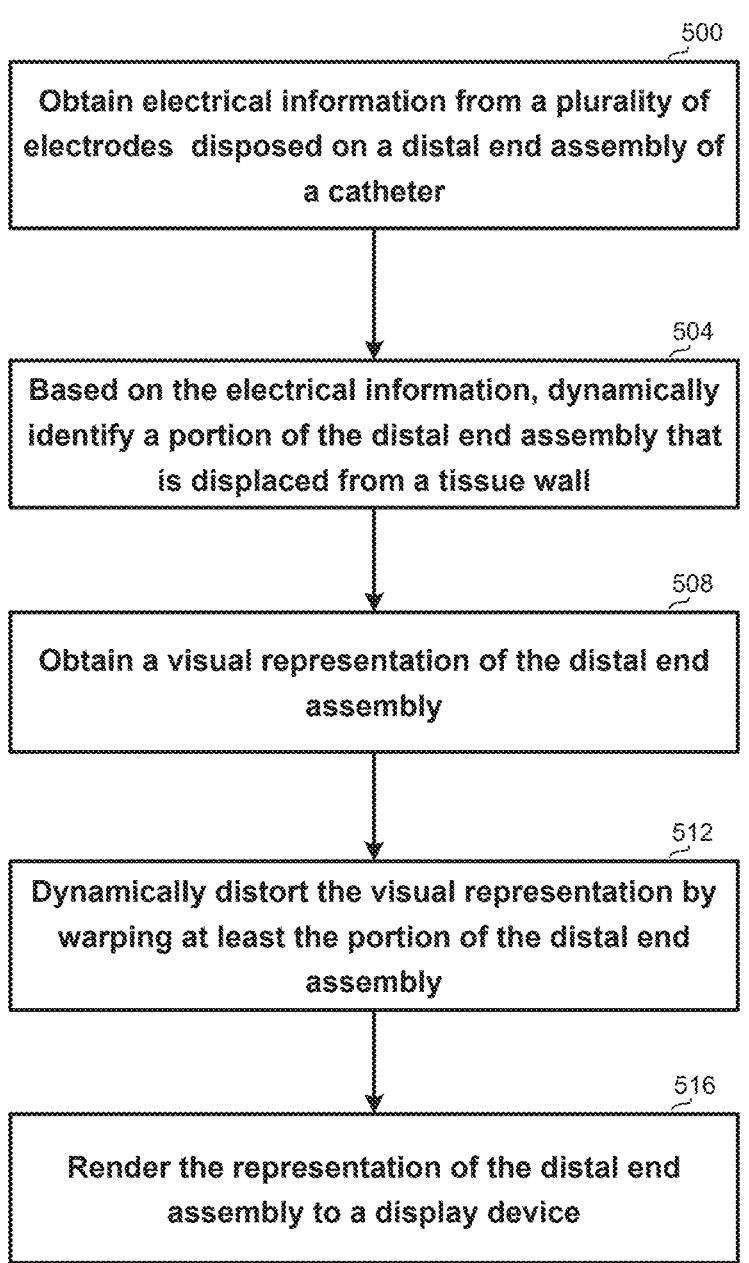

*500*

Obtain electrical information from a plurality of electrodes disposed on a distal end assembly of a catheter

*504*

Based on the electrical information, dynamically identify a portion of the distal end assembly that is displaced from a tissue wall

*508*

Obtain a visual representation of the distal end assembly

*512*

Dynamically distort the visual representation by warping at least the portion of the distal end assembly

*516*

Render the representation of the distal end assembly to a display device

FIG. 5

METHOD AND SYSTEM FOR ASSISTING A USER IN GUIDING A CATHETER DURING A CARDIAL OPERATION

FIELD OF THE DISCLOSURE

This disclosure relates to medical applications in general, and to a user interface for guiding a user navigating a catheter, in particular.

BACKGROUND OF THE DISCLOSURE

Multiple heart diseases may be diagnosed and/or treated using catheters. The catheter may be selected according to the task, for example a diagnostic catheter, an ablation catheter, or another catheter type.

Arrhythmias, for example, may be caused by problems with the electrical conduction system of the heart, and in particular electrical activity in one or more points or areas on a wall of a heart chamber. Atrial fibrillation is an arrhythmia characterized by disorganized signals that make the atria (left and/or right atria) squeeze very fast and in an asynchronous cardiac rhythm.

A common treatment of atrial fibrillation, also referred to as A-fib, is ablation which uses energy to create scars on one or more active areas on the heart wall, in order to block faulty electrical signals that contribute to the disorganized signals and to restore typical heartbeat. It may be convenient to build an electro-anatomical model of a heart chamber and also track location of the catheter within the modeled chamber. Additionally or alternatively, fluoroscopy may be used for determining the current location of the catheter such that ablation can be applied where it is most effective.

BRIEF DESCRIPTION OF THE DRAWINGS

The present disclosure will be more fully understood from the following detailed description of the examples thereof, taken together with the drawings, in which:

FIG. 4A is an illustration of an example virtual representation of the distal end assembly of a balloon catheter, in accordance with some exemplary embodiments of the disclosure;

FIG. 4B is an illustration of an example virtual representation of the distal end assembly of the balloon catheter that is displayed to a user while the distal end assembly is positioned at a second position within the heart, in accordance with some exemplary embodiments of the disclosure;

FIG. 5 is a flowchart of steps in a method for guiding a user in navigating a catheter during a cardiac operation, in accordance with some embodiments of the disclosure.

DETAILED DESCRIPTION OF EXAMPLES

Figure 1:
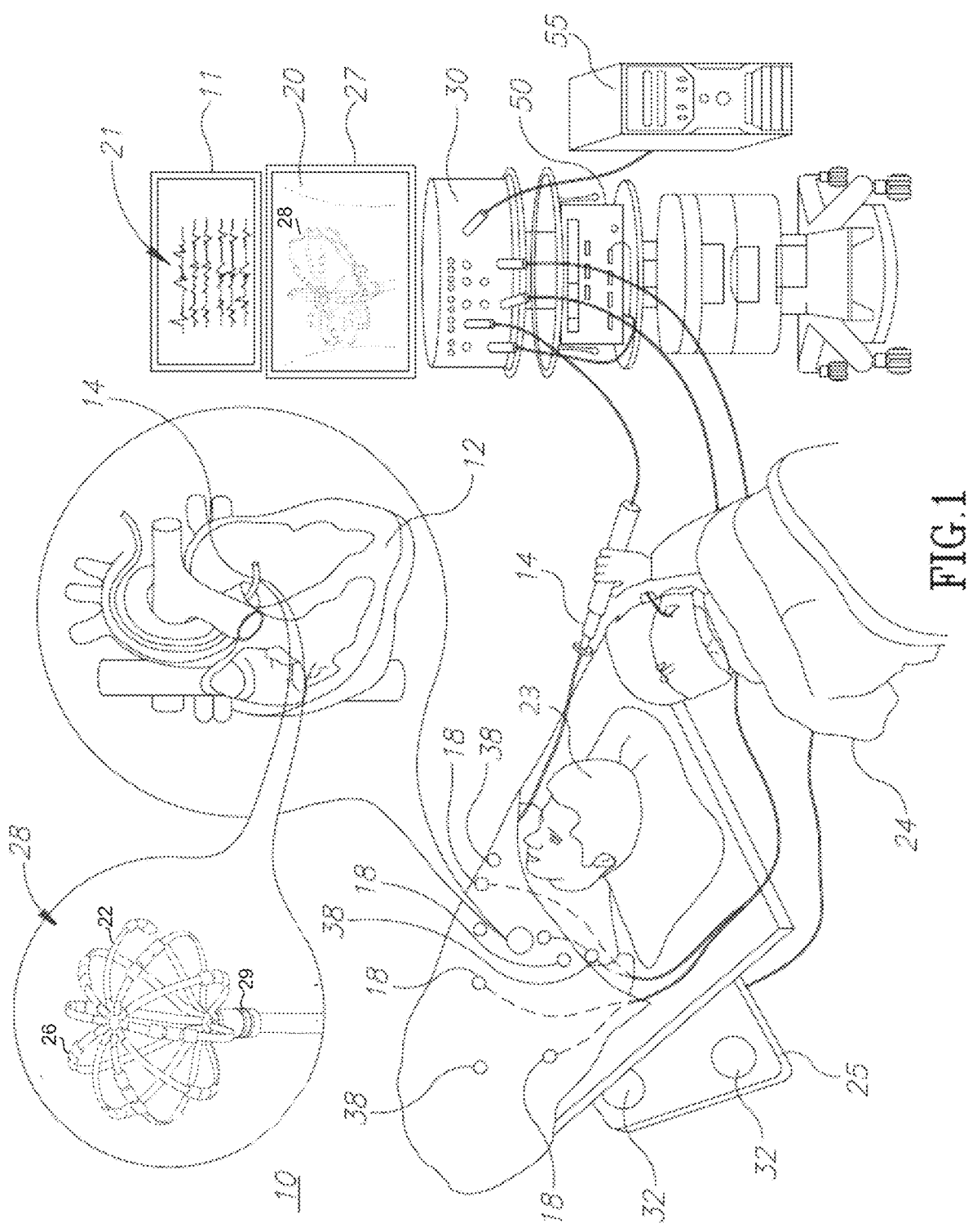
FIG. 1 is a schematic, pictorial illustration of a catheter-based electrophysiological (EP) mapping and ablation system, in accordance with some exemplary embodiments of the disclosure.

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

OVERVIEW

When conducting a diagnostic procedure and/or an ablation therapy with a catheter, a physician, must skillfully maneuver a distal end assembly of the catheter within the heart chamber to map the chamber and/or reach a location of interest, e.g., reach the pulmonary veins (PV). Care must be taken to avoid pressing the tissue wall with excessive pressure.

Prior to mapping or in the absence of mapping, the physician may not have visual guidance on where to maneuver the catheter. Traditionally, fluoroscopy is used for providing real-time imaging and tracking of movement of the target, in the form of a video of the heart and movements therein. Fluoroscopy passes X-rays through the body over a period of time, and naturally the longer the procedure, the higher dose of radiation needs to be applied. It is appreciated that fluoroscopy implies risks not only to the patient but also to the staff, including the physician.

Thus, it is beneficial to guide the physician to a location(s) of interest within a heart chamber, without, or with significantly reduced usage of fluoroscopy or other methods involving radiation or hazardous materials.

Thus, embodiments of the present disclosure provide a system and method for assisting the physician in navigating the catheter within a heart chamber and/or to the location of interest within the chamber, e.g. a location designated for treatment, such as the passage from atrium to the PV.

In some examples, a distal end assembly of a catheter, e.g., diagnostic and/or therapeutic catheter, may have an expandable configuration in the form of a balloon or a basket that comprises a plurality of splines. The distal end assembly may include a plurality of electrodes that are distributed in a 3D configuration, e.g., each spline of a basket catheter may carry one or more electrodes.

The electrodes may be connected to circuitry configured to track impedance in the vicinity of each of a plurality of the electrodes in real-time as the physician is navigating with the catheter. Optionally, a tissue proximity index (TPI) for each of a plurality of the electrodes may be tracked based on the impedance measurements.

When navigating the catheter within the chamber, e.g. and into a PV, it is desired that the distal end assembly does not press against the heart wall with excessive force, but rather advances in the direction of the inner space of the chamber, hereinafter referred to also as void.

In accordance with the disclosure, in the absence of adequate anatomical information, e.g., a model, map or image of the chamber and the location of the distal end assembly with respect to the anatomical structure of the chamber, a virtual representation of the distal end assembly may be displayed to the user over a display device. The visual representation may be visually manipulated in a manner that indicates a direction in which the catheter may be steered to avoid a tenting effect where the distal end assembly of the catheter pushes the heart wall, and to advance away from the wall and into the void. For example, the representation may include the distortion of the distal end assembly to indicate the direction.

In some examples, the distal end assembly may be displayed distorted in a schematic manner. For example, in a basket catheter the representation may show the same number of splines as comprised in the distal end assembly of the catheter, wherein one or more splines are warped, for example made elongated, enlarged, or "pulled" in the direction in which the distal end assembly should be moved. For a balloon catheter, the general shape may be "squashed", e.g., deflated or narrowed, at one or more areas. Thus, the representation may "direct" the user to navigate the catheter in the possible direction and away from the heart wall. A map of the heart may or may not be displayed with the distal end assembly shown therein.

In some embodiments, an estimated outline of the walls may be drawn, as mapping points are being collected by the distal end assembly.

Thus, the distal end assembly is displayed in an optionally non-realistic manner, since it is drawn schematically and distorted, for example one or more splines are warped, which of course does not happen to the actual spline. However, this non-realistic manner hints to the user how to steer the catheter to a required location.

In some examples, the distortion may be performed only when the catheter is in motion, and avoided when it is at rest. Thus, the user can get guidance when moving the catheter, but upon arriving to the required location, or otherwise stopping, it is displayed in a more realistic manner.

In some examples, the distortion may be performed subject to user's preference or setting, such that the user can toggle this feature on and off according to the user's preferences, which may change over the course of the operation.

SYSTEM DESCRIPTION

Reference is made to FIG. 1 showing an example catheter-based electrophysiology mapping and ablation system 10. System 10 includes multiple catheters, which may be percutaneously inserted by a physician 24 through the vascular system of a patient 23 into a chamber or vascular structure of a heart 12. Typically, a delivery sheath catheter is inserted into the left or right atrium near a desired location in heart 12. Thereafter, one or more catheters may be inserted into the delivery sheath catheter so as to arrive at the desired location in heart 12. The plurality of catheters may include catheters dedicated for sensing Intracardiac Electrogram (IEGM) signals, catheters dedicated for ablating and/or catheters dedicated for both sensing and ablating.

An example catheter 14 is illustrated herein. Physician 24 may place a distal end assembly 28 of catheter 14 within a blood pool or in contact with the heart wall for sensing different areas in heart 12. For example, for ablation, physician 24 may place a distal tip of an ablation catheter in contact with a target site for ablating tissue.

The term distal tip may be used interchangeably with the term distal end assembly.

Distal end assembly 28 of catheter 14 may comprise multiple electrodes 26 optionally distributed over a plurality of splines 22 configured to sense IEGM signals and/or to apply ablation energy at a location. Catheter 14 may additionally include a position sensor 29 embedded in or near distal end assembly 28 for tracking position and orientation of distal end assembly 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. The real time position of distal end assembly 28 of catheter 14 may be tracked based on magnetic fields generated with location pad 25 and sensed by magnetic based position sensor 29. Details of the magnetic based position sensing technology are described in U.S. Pat. Nos. 5,539,199; 5,443,489; 5,558,091; 6,172,499; 6,239,724; 6,332,089; 6,484,118; 6,618,612; 6,690,963; 6,788,967; 6,892,091.

Additionally or alternatively, system 10 may include one or more electrode patches 38 positioned for skin contact on patient 23 to establish location reference for location pad 25 as well as impedance-based tracking of electrodes 26. For impedance-based tracking, electrical current is directed to electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 may record and display electrograms 21 captured with body surface ECG electrodes 18 and IEGM captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more electrodes at a distal end assembly of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 may be configured to establish electrical communication between catheters, other electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software stored therein, and user interface capability. Workstation 55 may provide multiple functions, optionally including modeling the current position and orientation of the catheter or the distal end assembly thereof, determining the absolute or relative distance of each electrode from a tissue, calculating a distortion of one or more portions of the distal end assembly, and displaying on display device 27 a schematic illustration 20 of the catheter or the distal end assembly thereof, including the distortion, if applicable, and if desired by the user. In some embodiments, an outline of the tissue such as the heart wall, as estimated by the distances of the electrodes therefrom, may be displayed as well. One commercial product embodying elements of the system 10 is available as the CARTO™ 3 System, available from Biosense Webster, Inc., 31A Technology Drive, Irvine, CA 92618.

Figure 2:
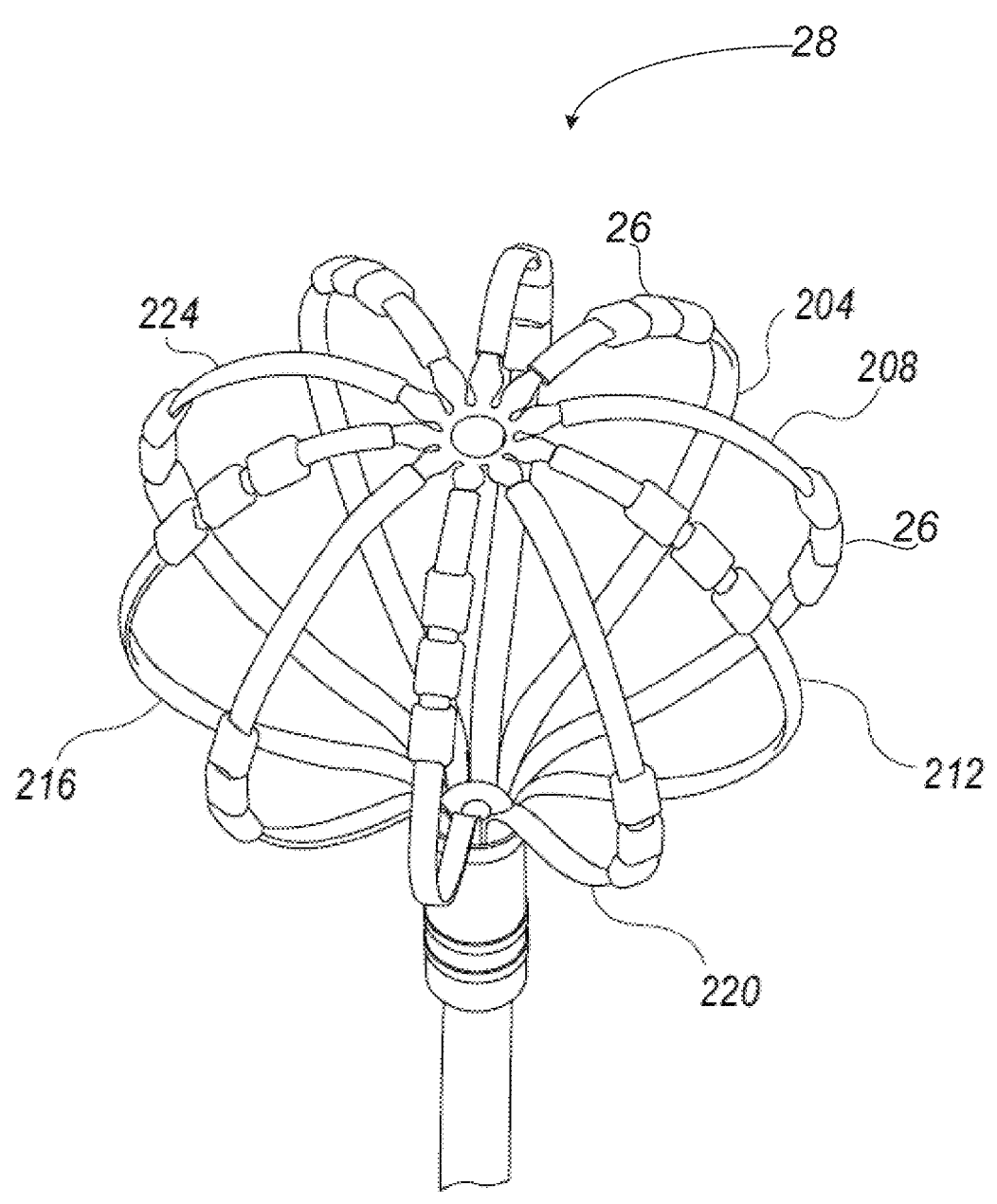
FIG. 2 is a schematic illustration an example distal head assembly of a catheter, in accordance with some exemplary embodiments of the disclosure.

Referring now to FIG. 2, showing a schematic illustration of a specific distal end assembly 28, in accordance with some exemplary embodiments of the disclosure. Distal end assembly 28 comprises 10 splines, such as splines 204, 208, 212, 216, 220 and 224 (all analogous to splines 22 of FIG. 1), each carrying a few electrodes 26. It is appreciated that catheter 14 and distal end assembly 28 are exemplary only, and the disclosure is equally applicable to other types of catheters.

Figure 3:
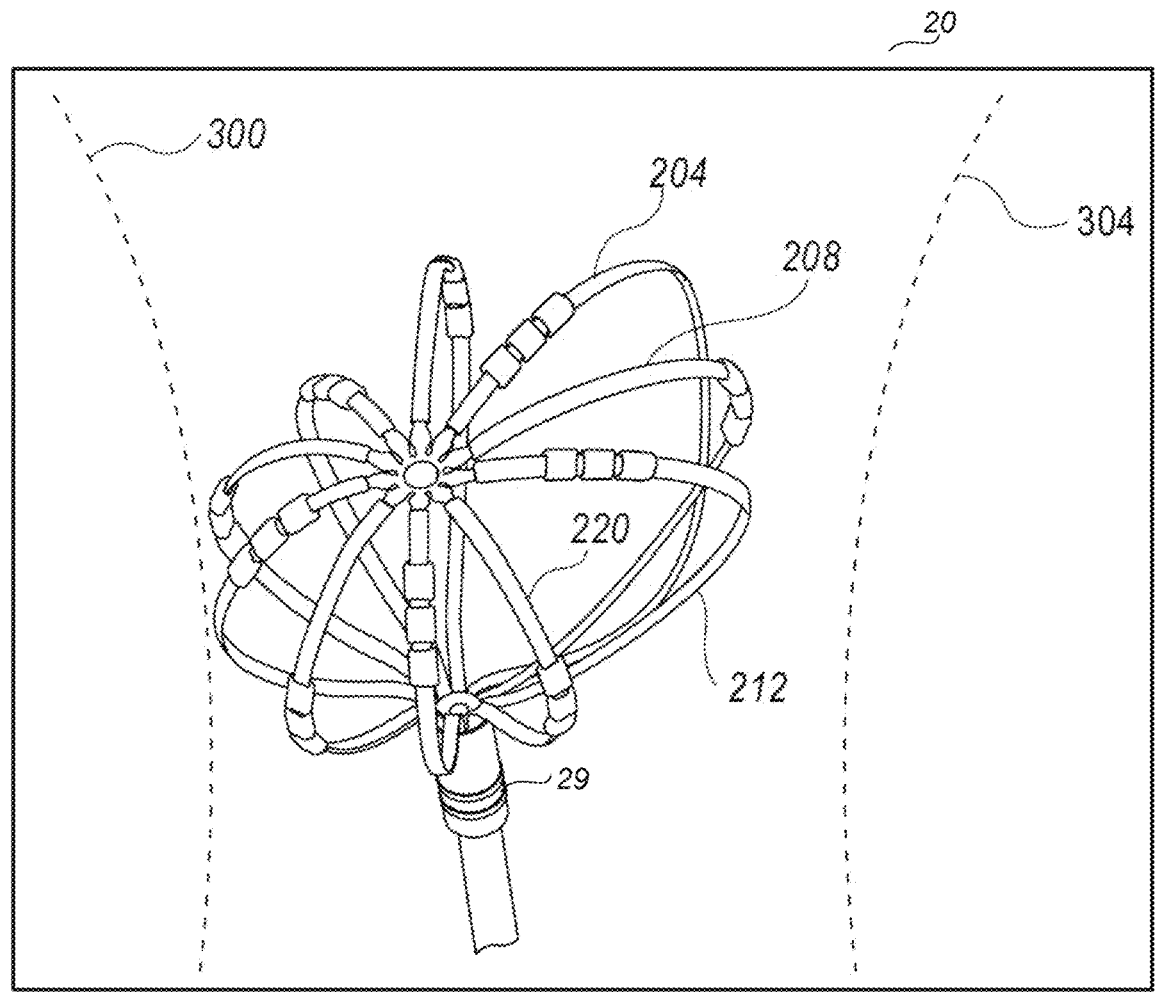
FIG. 3 is an illustration of an example virtual representation of the distal end assembly of a catheter that is displayed to a user while the distal end assembly is positioned at a first position within the heart, in accordance with some exemplary embodiments of the disclosure.

Referring now to FIG. 3, showing illustration 20, as may be presented over display device 27 to a user during an operation, in accordance with some exemplary embodiments of the disclosure.

Currently, without the use of fluoroscopy or similar techniques, an accurate map of the area of the heart is unavailable. Rather, an estimated map may be displayed, obtained, for example, based on prior knowledge, the distance of the electrodes from the walls and the known geometric relationship between the electrodes, previously applied fluoroscopy, or the like. Thus, walls 300 and 304 indicate the two-dimensional projection of the estimated shape of the area where distal end assembly 28 is currently present.

As shown in FIG. 3, distal end assembly 28 is closer to projected wall 300 than to projected wall 304, and thus needs to be steered by the physician in the direction of arrow 308, such that it moves from a narrower area to a wider space. Thus, it may be distorted such that the shape of one or more of the splines, such as splines 204, 208 and 212 are warped so as to indicate to the user the direction in which the catheter should be steered, in order to stay away from the heart wall and advance towards the larger space, i.e., the void. It is appreciated that arrow 308 may or may not be part of illustration 20.

Thus, spline 204 is warped in the direction of wall 304 to a certain degree, and splines 208, 212 and 220 are warped to lesser and lesser degrees, such that it appears that the splines are "pulled" in the direction where distal end assembly 28 is to be directed.

It is appreciated that the actual shape of distal end assembly 28 is unchanged, and it is just a visualization that is being manipulated to direct the user in the desired direction, absent an accurate map of the heart and the accurate location of distal end assembly 28 therein.

It is appreciated that this is merely an example, and other representations may be used. For example, the splines may be warped in the opposite direction, such that it appears that they are closer to the wall and should be steered away.

In further examples, one or more arrows may be displayed in proximity to the visual representation of the distal end assembly, wherein the arrow may indicate the required or possible direction, instead of or in addition to distorting the visual representation of the distal end assembly, or the like.

Referring now to FIGS. 4A and 4B. FIG. 4A shows a balloon type catheter distal end assembly 404, in accordance with some exemplary embodiments of the disclosure. FIG. 4B shows an illustration of an example virtual representation of distal end assembly 408 of the balloon catheter as may be displayed to a user when passing through a narrow area, in accordance with some exemplary embodiments of the disclosure. Thus, balloon type catheter distal end assembly 408 is the same as ballon type catheter distal end assembly 404 when passing through a narrow area. The area may be surrounded by a wall, projected as walls 408 and 412. In order to direct the physician not to press against the wall, balloon type catheter distal end assembly 408 is squashed, e.g. flattened or narrowed at its middle, thus suggesting that movement is possible in the up and down direction. Accordingly, arrows 420 and 424 are optionally displayed to indicate these directions.

Thus, viewing the illustrated distal end of the distal end assembly, the user can get a perception of the position and orientation of the distal end assembly relative to the surrounding tissues, and thereby to the available direction in which the catheter may be steered, without having to use fluoroscopy.

It is appreciated that the method can be used during some parts of the operation, such that fluoroscopy can be used for shorter periods of time thereby reducing the amount of radiation and the risk to the patient and to the staff. For example fluoroscopy may be used only when it is required to navigate in smaller areas, upon arrival at the ablation site, or the like.

Referring now to FIG. 5, showing a flowchart of steps in a method for guiding a user of a catheter during cardiac operations, in accordance with some exemplary embodiments of the disclosure.

At step 500, electrical information, such as impedance or TPI may be obtained from a plurality of electrodes disposed over a distal end assembly of a catheter. Impedance may be measured based on transmitting a signal between electrodes on the distal end assembly, or based on transmitting a signal between the electrodes on the distal end assembly and a reference electrode. The reference electrode may be located on the distal end assembly of the shaft of the catheter or on the patient's skin. The catheter may be any basket type catheter, balloon type catheter, or expandable catheters.

At step 504, based on the electrical information, a portion of the distal end assembly may be identified which is displaced from the tissue wall. In some examples, a distance between each electrode and the nearest tissue may be determined, and one or more portions may be selected based upon the distances. In some examples, the distances may be absolute, for example in mm, micron, or the like, wherein the distance of the electrode nearest the tissue wall needs to exceed a predetermined threshold. In other examples, the distance may be relative, for example the distance between the farthest electrode from the nearest location on a tissue may be 1.7 times the distance between the second farthest electrode and a corresponding nearest location. It is appreciated that as some electrodes may be adjacent to each other, the distance may be calculated for a group of electrodes.

At step 508, a visual representation of the distal end assembly may be obtained. The representation may be calculated dynamically, obtained from a storage device, previously created and loaded, or the like.

The representation may be in three dimensions, such that although it is projected onto a two-dimensional plane, when the user rotates the view, the representation updates automatically to indicate the projection over the changing viewing plane.

The representation may be schematic, e.g., in a basket-type catheter it may display the correct number of splines, with an indication of the electrodes, such as a circle, marked at the proportional locations over the spline.

At step 512, the representation may be distorted, for example by warping at least the displaced portion of the distal end assembly. Distorting may refer to elongating or enlarging the relevant portion. For example, one or more of the splines of a basket-type catheter may be warped, e.g., appear as pulled in the direction in which the catheter should be moved, whether towards the void or towards the tissue. In another example, the shape of a balloon type catheter may be squashed for example by narrowing or deflating.

It is appreciated that multiple splines a basket-type catheter may be warped in different angles and to different degrees, as shown for example in FIG. 3 where spline 204 is warped more, and in a sharper angle, than spline 208. The degree and direction of the warping may be determined upon the closeness of the spline direction with the required direction, the distance from the walls, or the like.

In another example, a balloon type catheter may appear partly or fully squashed to indicate its closeness to the walls.

At step 516, the representation may be rendered to a display device, including projecting the three dimensional information onto a two dimensional plane.

In some examples, based upon the distances, an available direction in which the catheter may be steered is determined, e.g., calculated. The direction should be towards a void and/or in which the distal end assembly of the catheter is free to advance. In some example embodiments, the direction determined may be toward an ostium of a pulmonary vein. In other situations, for example when the user wants to perform an ablation, the direction determined based upon the distances may be a direction that steers the distal end assembly towards the tissue.

In some examples, the outline of the tissue in the vicinity of the catheter may be estimated based upon the distances from the electrodes, and rendered as well, such that the user can get a feeling of the location of the catheter relative to the walls. In some examples, estimating the outline of the tissue may also use prior knowledge about the structure of the patient's heart, as may have been obtained earlier.

In some examples, the distal end assembly as warped may be rendered on the display together with fluoroscopy. The distal end assembly as warped may be rendered together with the anatomical map, to provide guidance to the user as to the direction in which the catheter is to be steered.

The user may have an option enabled through a user interface, whether to eliminate the warped representation option, and continue using fluoroscopy or other methods, or whether to use this option of indicating the direction. It is appreciated that the user may toggle this option on and off as the user wishes.

In some examples, the user may also select whether to activate this option continuously, or only when the catheter is being moved.

In some examples, if the user wishes to use the option, the user may further indicate whether the user wishes to warp the representation of the catheter such that it seems like it is directed towards the void or towards the tissue.

If an anatomical map is available, the distal end assembly may be represented at its accurate location over the map, as obtained for example from electrode 29.

In some examples, if it is estimated that the distal end assembly is too close, for example the distance between the distal end assembly and the heart wall is below a threshold, or even when the distal end assembly presses against the heart wall, an audio indication may be played to warn the physician.

It is appreciated that the disclosure may also be used for mapping purposes. When mapping, it is required to collect location information of points within the chamber and along the tissue wall, while avoiding tenting, which may occur when the distal end assembly pushes the tissue wall out. Collecting points in this situation will result in the chamber appearing larger than it is due to the stretching. Thus, it is important to visually indicate to the user the directions in which the distal end assembly can be moved without pressing the tissue wall.

Figure 6:
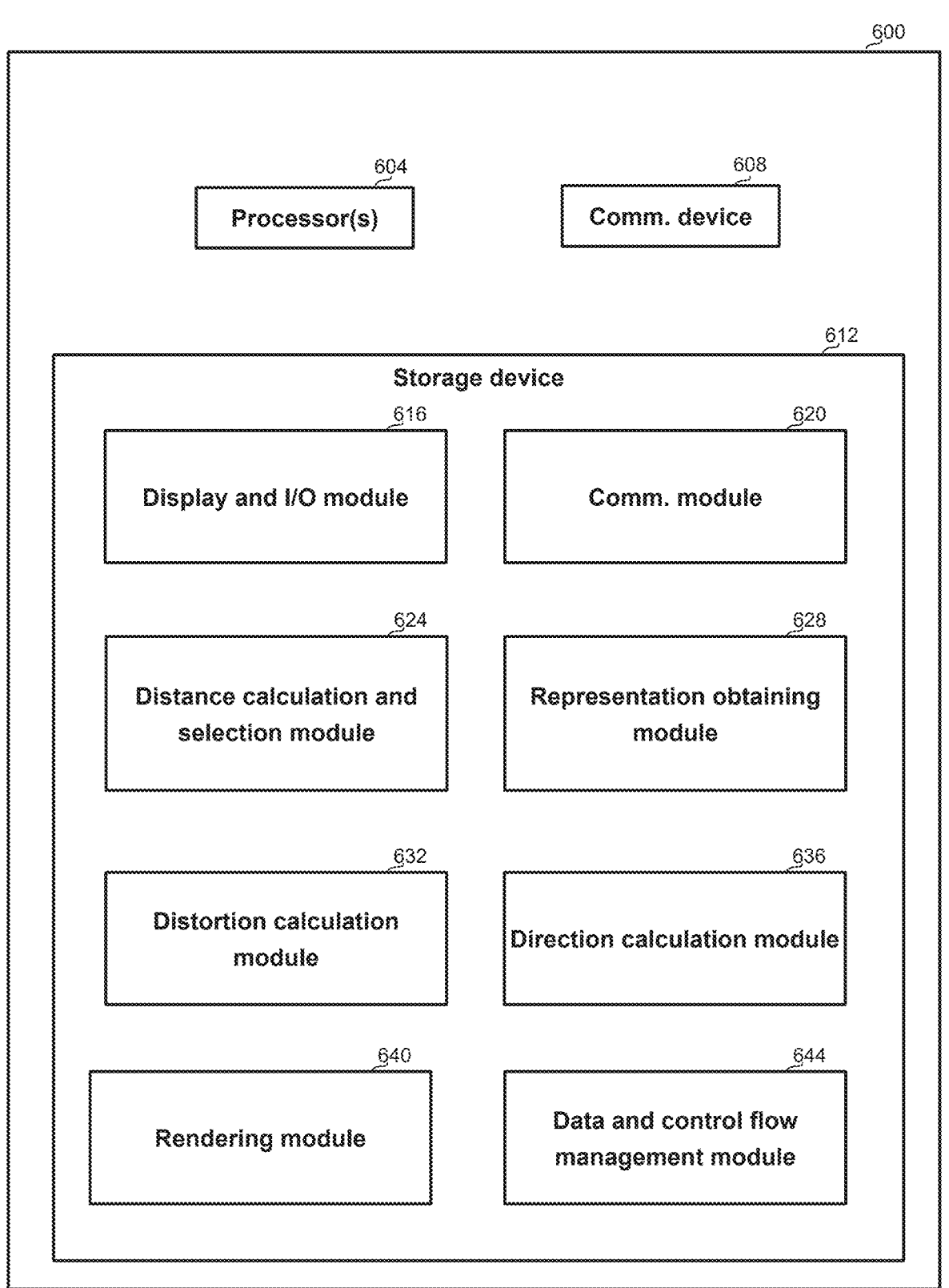
FIG. 6 is a schematic block diagram of a computing platform for guiding a user in navigating a catheter during a cardiac operation, in accordance with some exemplary embodiments of the disclosure.

Referring now to FIG. 6, showing a block diagram of a computing platform 600 for guiding a user in navigating a catheter during a cardiac operation, in accordance with some exemplary embodiments of the disclosure.

It will be appreciated that computing platform 600 may be embedded within workstation 55, but may also be a stand-alone computing platform or embedded elsewhere and be in operative communication with workstation 55.

Computing platform 600 may be implemented as one or more computing platforms which may be operatively connected to each other. For example, one or more remote computing platforms, which may be implemented for example on a cloud computer. Other computing platforms may be a part of a computer network of the associated organization. In other embodiments, all the functionality may be provided by one or more computing platforms all being a part of the organization network.

Computing platform 600 may comprise one or more processors 604 located on the same computing platform or not, which may be one or more Central Processing Units (CPU), microprocessors, electronic circuits, Integrated Circuits (IC) or the like. Processor 604 may be configured to provide the required functionality, for example by loading to memory and activating the software modules stored on storage device 612 detailed below.

Computing platform 600 may comprise a communication device 608 for communicating with other devices or other computing platforms, for example obtaining information from the catheterization controller, storing and retrieving data to or from remote storage devices, or the like. Communication module 608 may be adapted to interface with any communication channel such as Local Area Network (LAN), Wide Area Network (WAN), cellular network or the like, and use any relevant communication protocol.

Computing platform 600 may comprise a storage device 612, such as a hard disk drive, a Flash disk, a Random Access Memory (RAM), a memory chip, or the like. In some exemplary embodiments, storage device 612 may retain program code operative to cause processor 604 to perform acts associated with any of the modules listed below, or steps of the method of FIG. 5 above. The program code may comprise one or more executable units, such as functions, libraries, standalone programs or the like, adapted to execute instructions as detailed below.

Alternatively or additionally, the provided instructions may be stored on non-transitory tangible computer-readable media, such as magnetic, optical, or electronic memory.

Storage device 612 may comprise display and I/O module 616, for rendering a display to the user to be displayed over display device 27, such as the illustration of the catheter or the distal end assembly thereof, the outline of the walls, an anatomical map if available, or the like.

Display and I/O module 616 may also be operative in receiving instructions and operation parameters from the user, such as whether to activate the catheter display or use fluoroscopy (or other methods) instead, whether to warp the splines at all times or only when the catheter is moving, whether to distort the catheter in the direction of the void or the tissue, or the like.

Storage device 612 may comprise communication module 620 for transmitting and receiving data to and from other systems, such as the ablation system, external storage devices, or the like. For example, communication module 620 may be operative for receiving information from the various electrodes, such as impedance, TPI, or the like.

Storage device 612 may comprise distance calculation and selection module 624, for calculating a distance between each portion of the distal end assembly, such as electrode, group of electrodes, one or more splines, or the like, and the nearest point in the tissue. The distance may be absolute or relative. It is appreciated that as some electrodes may be adjacent to each other, the distance may be calculated for a group of electrodes, together referred to as an "electrode". Based upon the distances, a portion of the distal end assembly that is farthest from the tissue wall may be selected.

Storage device 612 may comprise representation obtaining module 628, for generating a visual representation of the distal end assembly. The visual representation may be calculated earlier during the operation, calculated dynamically, received from a storage device, or the like.

Storage device 612 may comprise distortion calculation module 632. Distortion calculation module 628 may be configured to determine whether and how to distort at least the portion of the distal end assembly farthest from the tissue wall, for example in the case of a basket catheter, distortion calculation module 632 may determine the warping degree, direction and location over the spline of one or more splines according to the distance of the electrodes from the tissue and to the direction. For example, the spline having an electrode farthest from the tissue and closest to the void may be distorted such that it is warped towards the void, and "pulls" the catheter in that direction, thus it is appreciated that two or more splines may be warped in different manners or degrees.

In some examples, a spline having disposed thereon an electrode that is in contact with the tissue may appear flattened, to indicate that it is pressed against the tissue.

Representation calculation module 628 may be further configured to calculate an outline of the wall, according to the distances of the electrodes from the tissue, and the known spatial relationships between the locations of the electrodes.

Storage device 612 may comprise direction calculation module 636 for determining a direction in which the catheter should be steered.

Storage device 612 may comprise rendering module 640 for rendering to a 2D device the representation of the catheter, with the distorted portions, and optionally the tissue outline, an arrow indicating the direction, a map of the heart chamber, or the like.

Storage device 612 may comprise data and control flow management module 644, for operating the above modules as required, for example providing the distorted representation if the user so indicates using a user interface control and avoiding otherwise, distorting the catheter illustration according to the user's preferences, or the like.

It is appreciated that the steps and modules disclosed above are in addition to the software, hardware, firmware or other modules required for operating a catheter, or the like. Further details for methods and systems may be found, for example in U.S. Pat. Nos. 8,676,305, 9,629,567, incorporated herein by reference in their entirety for any purpose.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture instructions, machine instructions, machine dependent instructions, microcode, firmware instructions, state-setting data, or either source code or object code written in any combination of one or more programming languages, programming languages such as Java, C, C++, Python, or others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

A method comprising:

obtaining electrical information from a plurality of electrodes disposed on a distal end assembly of a catheter within a heart of a patient as the catheter is being maneuvered within the heart;

dynamically identifying a portion of the distal end assembly that is displaced from tissue wall of the heart, based upon the electrical information received from the plurality of electrodes;

generating a visual representation of the distal end assembly;

dynamically distorting the visual representation by warping (the identified portion of the distal end assembly; and rendering the visual representation as dynamically distorted to the display device.

Example 2

The method according to example 1, wherein the portion is identified as being displaced from the tissue wall in at least a predetermined threshold.

Example 3

The method according to example 1, wherein the portion is identified as being displaced from the tissue wall further than other portions of the distal end assembly.

Example 4

The method according to example 1, wherein the representation is calculated in three dimensions.

Example 5

The method according to example 1, wherein the electrical information is impedance.

Example 6

The method according to example 1, wherein the catheter is a basket-type catheter comprising a plurality of splines on which the electrodes are disposed, and wherein distorting the representation comprises warping at least one spline from the plurality of splines.

Example 7

The method according to example 1, wherein the catheter is a balloon-type catheter and wherein distorting the representation comprises deflating or narrowing at least one portion of the balloon-type catheter.

Example 8

The method according to example 1, wherein distorting the representation is performed subject to the catheter being in motion within the heart.

Example 9

The method according to example 1, wherein during ablation of a tissue of the patient, the visualization of the distal end assembly is rendered without distortion.

Example 10

The method according to example 1, wherein distorting the representation is subject to user selection.

Example 11

The method according to example 1, further comprising tracking locations and orientations of the distal end assembly.

Example 12

The method according to example 1, further comprising generating a map of a heart chamber based on the locations of the distal end assembly within the heart chamber, and wherein the visualization of the distal end assembly as distorted is rendered on the map at a current location of the distal end assembly.

Example 13

The method according to example 12, wherein said tracking is performed using a magnetic position tracking.

Example 14

The method according to example 1, further comprising determining a direction in which the catheter is to be steered, and rendering a visual indication of the direction in proximity to the visual representation of the distal end assembly.

Example 15

The method according to example 1, further comprising rendering an estimated outline of the tissue wall in the vicinity of the distal end assembly.

Example 16

The method according to example 15, wherein the outline is estimated based on the distance of each electrode from the tissue wall.

Example 17

A computerized apparatus having a processor coupled with a memory unit, the processor being adapted to perform the steps of:
obtaining electrical information from a plurality of electrodes disposed on a distal end assembly of a catheter within a heart of a patient as the catheter is being maneuvered within the heart;
dynamically identifying a portion of the distal end assembly that is displaced from tissue wall of the heart, based upon the electrical information received from the plurality of electrodes;
generating a visual representation of the distal end assembly;

dynamically distorting the visual representation by warping (the identified portion of the distal end assembly; and
rendering the visual representation as dynamically distorted to the display device.

Example 18

The computerized apparatus according to example 17, wherein the catheter is a basket-type catheter comprising a plurality of splines on which the electrodes are disposed, and wherein distorting the representation comprises warping at least one spline from the plurality of splines.

Example 19

The computerized apparatus according to example 17, wherein the catheter is a balloon-type catheter and wherein distorting the representation comprises deflating or narrowing at least one portion of the balloon-type catheter.

Example 20

A computer program product comprising a non-transitory computer readable medium retaining program instructions, which instructions when read by a processor, cause the processor to perform:
obtaining electrical information from a plurality of electrodes disposed on a distal end assembly of a catheter within a heart of a patient as the catheter is being maneuvered within the heart;
dynamically identifying a portion of the distal end assembly that is displaced from tissue wall of the heart, based upon the electrical information received from the plurality of electrodes;
generating a visual representation of the distal end assembly;
dynamically distorting the visual representation by warping (the identified portion of the distal end assembly; and
rendering the visual representation as dynamically distorted to the display device.

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:
1. A method comprising:
obtaining electrical information from a plurality of electrodes disposed on a distal end assembly of a catheter within a heart of a patient as the catheter is being maneuvered within the heart;
dynamically identifying a portion of the distal end assembly that is displaced from tissue wall of the heart, based upon the electrical information received from the plurality of electrodes;
generating a visual representation of the distal end assembly;

dynamically distorting the visual representation by stretching a shape of the identified portion of the distal end assembly in a manner that provides a visual indication of a direction extending outwardly from the portion identified, wherein the direction extending outwardly from the portion identified is the direction available for steering the distal end assembly away from the tissue wall or along the tissue wall; and rendering the visual representation as dynamically distorted to a display device.

2. The method of claim 1, wherein the portion is identified as being displaced from the tissue wall in at least a predetermined threshold.

3. The method of claim 1, wherein the portion is identified as being displaced from the tissue wall further than other portions of the distal end assembly.

4. The method of claim 1, wherein the visual representation is calculated in three dimensions.

5. The method of claim 1, wherein the electrical information is impedance.

6. The method of claim 1, wherein the catheter is a basket-type catheter comprising a plurality of splines on which the plurality of electrodes is disposed, and wherein distorting the shape of the visual representation comprises stretching the shape of the visual representation of at least one spline from the plurality of splines.

7. The method of claim 1, wherein the catheter is a balloon-type catheter and wherein distorting the visual representation further comprises deflating or narrowing at least one portion of the visual representation of the balloon-type catheter.

8. The method of claim 1, wherein distorting the visual representation is performed based on determining that the catheter is in motion within the heart.

9. The method of claim 1, wherein during ablation of a tissue of the patient, the visual representation of the distal end assembly is rendered in its known shape without the imposed distorting.

10. The method of claim 1, wherein distorting the representation is subject to user selection.

11. The method of claim 1, further comprising tracking locations and orientations of the distal end assembly.

12. The method of claim 11, further comprising generating a map of a chamber of a heart based on the locations of the distal end assembly within the chamber of the heart, and wherein the visual representation is rendered on the map at a current location of the distal end assembly.

13. The method of claim 11, wherein said tracking is performed using a magnetic position tracking system.

14. The method of claim 1, further comprising determining a direction in which the catheter is to be steered, and rendering a visual indication of the direction in proximity to the visual representation of the distal end assembly.

15. The method of claim 1, further comprising rendering an estimated outline of the tissue wall in the vicinity of the distal end assembly.

16. The method of claim 15, wherein the outline is estimated based on the distance of each electrode of the plurality of electrodes from the tissue wall.

17. A computerized apparatus having a processor coupled with a memory unit, the processor being adapted to perform the steps of:

obtaining electrical information from a plurality of electrodes disposed on a distal end assembly of a catheter within a heart of a patient as the catheter is being maneuvered within the heart;

dynamically identifying a portion of the distal end assembly that is displaced from tissue wall of the heart, based upon the electrical information received from the plurality of electrodes;

generating a visual representation of the distal end assembly;

dynamically distorting the visual representation by stretching a shape of the identified portion of the distal end assembly in a manner that provides a visual indication of a direction extending outwardly from the portion identified, wherein the direction extending outwardly from the portion identified is the direction available for steering the distal end assembly away from the tissue wall or along the tissue wall; and rendering the visual representation as dynamically distorted to a display device.

18. The apparatus of claim 17, wherein the catheter is a basket-type catheter comprising a plurality of splines on which the plurality of electrodes is disposed, and wherein distorting the shape of the visual representation comprises stretching the visual representation of at least one spline from the plurality of splines.

19. The apparatus of claim 17, wherein the catheter is a balloon-type catheter and wherein distorting the visual representation further comprises deflating or narrowing at least one portion of the visual representation of the balloon-type catheter.

20. A computer program product comprising a non-transitory computer readable storage medium retaining program instructions configured to cause a processor to perform actions, which program instructions implement:

obtaining electrical information from a plurality of electrodes disposed on a distal end assembly of a catheter within a heart of a patient as the catheter is being maneuvered within the heart;

dynamically identifying a portion of the distal end assembly that is displaced from tissue wall of the heart, based upon the electrical information received from the plurality of electrodes;

generating a visual representation of the distal end assembly;

dynamically distorting the visual representation by stretching a shape of the identified portion of the distal end assembly in a manner that provides a visual indication of a direction extending outwardly from the portion identified, wherein the direction extending outwardly from the portion identified is the direction available for steering the distal end assembly away from the tissue wall or along the tissue wall; and rendering the visual representation as dynamically distorted to a display device.

* * * * *